(12) United States Patent
Wang et al.

(10) Patent No.: US 9,114,233 B2
(45) Date of Patent: Aug. 25, 2015

(54) METHOD AND APPARATUS FOR MANAGING STRESS

(75) Inventors: Jia Wang, Shenzhen (CN); Jianbin Liu, Shenzhen (CN); Jiwei Zhao, Shenzhen (CN)

(73) Assignee: Oakwell Distribution, Inc., King of Prussia, PA (US)

( * ) Notice: Subject to any disclaimer, the term of this patent is extended or adjusted under 35 U.S.C. 154(b) by 809 days.

(21) Appl. No.: 13/310,509

(22) Filed: Dec. 2, 2011

(65) Prior Publication Data

US 2013/0144111 A1    Jun. 6, 2013

(51) Int. Cl.
  *A61M 21/02*  (2006.01)
  *A61B 5/024*  (2006.01)
  *A63B 23/18*  (2006.01)
  *A61M 21/00*  (2006.01)

(52) U.S. Cl.
  CPC ............ *A61M 21/02* (2013.01); *A61B 5/02405* (2013.01); *A61B 5/02416* (2013.01); *A63B 23/185* (2013.01); *A61M 2021/0088* (2013.01); *A61M 2205/584* (2013.01); *A61M 2230/06* (2013.01); *A61M 2230/435* (2013.01); *A63B 2230/04* (2013.01); *A63B 2230/062* (2013.01); *A63B 2230/208* (2013.01)

(58) Field of Classification Search
  CPC .......... A61M 21/02; A61M 2230/04–2230/06; A63B 23/185; A61B 5/024–5/0255
  USPC ...................... 600/26–28, 500–507
  See application file for complete search history.

(56) References Cited

U.S. PATENT DOCUMENTS

| | | | |
|---|---|---|---|
| 5,851,178 A * | 12/1998 | Aronow ........................ | 600/323 |
| 6,358,201 B1 * | 3/2002 | Childre et al. ................ | 600/300 |
| 7,117,032 B2 | 10/2006 | Childre | |
| 7,163,512 B1 | 1/2007 | Childre ......................... | 600/500 |
| 7,255,672 B2 | 8/2007 | Elliott ............................ | 600/27 |
| 7,462,151 B2 | 12/2008 | Childre ......................... | 600/300 |
| 7,497,821 B2 | 3/2009 | Elliott ............................ | 600/27 |
| 7,713,212 B2 | 5/2010 | Elliott .......................... | 600/500 |
| 2005/0124906 A1 * | 6/2005 | Childre et al. ............... | 600/529 |
| 2006/0047202 A1 * | 3/2006 | Elliott ........................... | 600/485 |
| 2010/0004519 A1 * | 1/2010 | Lamego et al. .............. | 600/310 |

* cited by examiner

*Primary Examiner* — Catherine B Kuhlman
(74) *Attorney, Agent, or Firm* — Miller Law Group, PLLC

(57) ABSTRACT

A stress management device is formed in an integrated design that enables pulse measurement, display of results and a power supply gathered into a small finger clip device. The stress management device includes a non-invasive infrared sensor that identifies and measures pulse rate variability and utilizes that information to calculate the power spectrum distribution and create a curve of the results multiple times per second. The device incorporates a display screen on which a graphic image of a pair of lungs filling and emptying to encourage the user into a predetermined breathing pattern known to reduce stress levels during a training period. After the completion of the training period, the device presents a score reflecting the percentage of times the user achieved high, medium and low relaxation states, and a pie chart reflecting the distribution of the states of relaxation calculated during the training period.

23 Claims, 7 Drawing Sheets

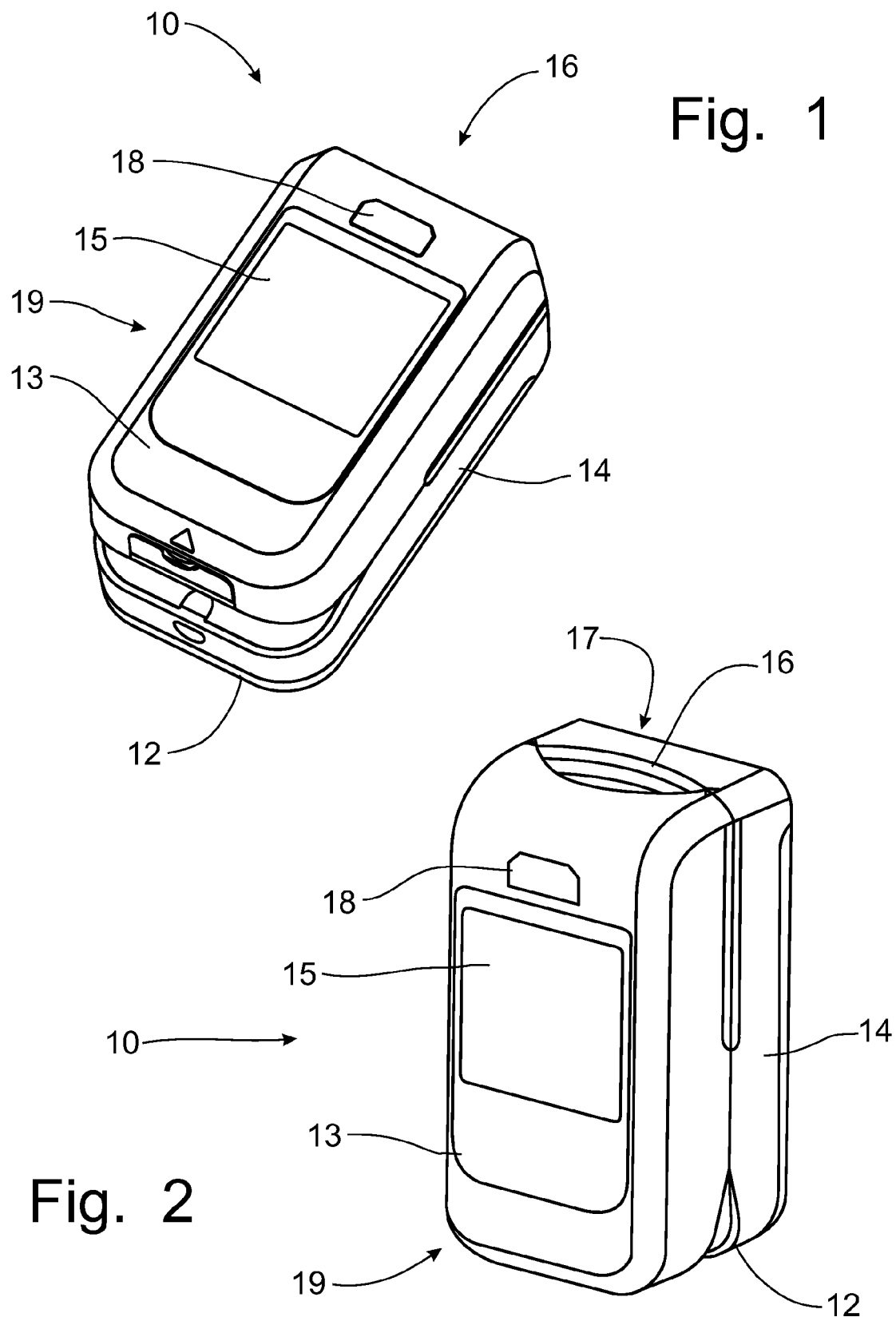

METHOD AND APPARATUS FOR MANAGING STRESS

FIELD OF THE INVENTION

The present invention relates generally to the management of stress through the inducement of relaxation and, more specifically, to an apparatus and a method of using that apparatus to guide the respiratory rate of the user of the apparatus to achieve a state of relaxation.

BACKGROUND OF THE INVENTION

Being subjected to stress has been shown to cause adverse mental and physical results in people. As a result, people have been trying to develop new methods and practices that will relieve stress and, as a consequence, induce a state of relaxation. Various stress-relieving practices have been developed over the years, from yoga techniques, to devices that massage various areas of the body, and to electronic devices that intend to control the breathing patterns of a user of the device, and thus indirectly revise the user's heart rate, to create a state of peaceful relaxation. Such electronic devices have been marketed under the brand names of emWave® Coherence Systems, emWave® Personal Stress Reliever and StressEraser® biofeedback system.

It has been found that the human body can achieve a state of relaxation by utilizing controlled breathing techniques, such as slow, steady and deep breathing, which in turn, slows and stabilizes the heart rate and induces a state of relaxation. One commonly utilized breathing rate for achieving relaxation has been six breathes per minute accomplished in a steady rhythm. However, breathing at the rate of six breaths per minute is not a normal breathing rate for many people. As a result, most people need to be trained and guided into such a breathing pattern.

The stationary condition of breathing and the trend of heart rate variation reflect the status of interaction between the sympathetic and parasympathetic neural system in the human body. When heart rate variation becomes regular and synchronized with the breathing rhythm, it is considered that the neural system tends to be in harmony with the body and mind, which means that the physical body becomes more effective, emotions are stabilized, and the mind is peaceful and perceptive, which is referred to as a highly physiological relaxed state. On the contrary, stressful emotions including anger, disappointment, and anxiety make the heart rate variation irregular and incoherent with breathing. In such cases, a stress management device can be utilized to guide the user to conduct slow and deep breaths, thus helping the user to focus his/her attention to enter into a relaxed state with body and mind harmony.

U.S. Pat. No. 6,358,201, issued on Mar. 19, 2002, to Doc L. Childre, et al, discloses a method of determining the state of entrainment between biological systems which undergo rhythmic functions, such as a breathing and heart rates, by determining a heart rate variability, and an apparatus for monitoring the heart beat of a user for application of that method. This Childre patent defines formulas to calculate a parameter of the frequency distribution and then outputs that parameter on the display of the apparatus to assist the user in attaining relaxation. Several divisional patents have also been granted from this U.S. Pat. No. 6,358,201, including U.S. Pat. No. 7,117,032, granted on Oct. 3, 2006; U.S. Pat. No. 7,163,512, granted on Jan. 16, 2007; and U.S. Pat. No. 7,462,151, granted on Dec. 9, 2008.

In U.S. Pat. No. 7,117,032, the apparatus defines one or more optimal breathing patterns for the user and then provides feedback to the user to reflect how closely the actual breathing pattern of the user matches the optimal breathing pattern defined by the apparatus. U.S. Pat. No. 7,163,512 defines the manner in which psychological coherence is indicated by the power spectrum distribution having a peak above a predetermined amplitude with the heart rate achieving a sine wave pattern, while U.S. Pat. No. 7,462,151 defines the indication of psychological coherence as when the power spectrum distribution is above a predetermined amplitude with total energy being above and below the peak, thus defining different aspects of the method of facilitating physiological coherence utilizing respiration training and autonomic balance.

An apparatus utilizing a method of presenting audible and visual cues to synchronize a user's breathing cycle with an external timing reference to synchronize heart rate variability with the user's breathing cycle is disclosed in U.S. Pat. No. 7,255,672, granted to Stephen B. Elliott on Aug. 14, 2007, and in U.S. Pat. No. 7,497,821, granted to Stephen B. Elliott on Mar. 3, 2009. A similar method and system for consciously synchronizing the breathing cycle with the natural heart rate cycle is disclosed in U.S. Pat. No. 7,713,212, issued to Stephen B. Elliott on May 11, 2010.

It would be desirable to provide a compact apparatus that can be mounted on the user's finger to measure heart rate, and sense breathing patterns, then display animation to guide the user into a breathing pattern that will induce a state of relaxation in the user. It would also be desirable that this apparatus evaluate the status of relaxation in the user and provide a respiratory feedback control to guide the user into the desired respiratory rate for achieving a state of relaxation. It would further be desirable to provide motivation to the user to continue utilizing the respiratory pattern for achieving a state of relaxation by providing the user with a visual display of the user's efforts in reaching a state of relaxation, as well as a score reflecting the success of the user's efforts.

SUMMARY OF THE INVENTION

It is an object of this invention to overcome the disadvantages of the prior art by providing a stress management device that is operable to measure stress through sensing pulse rates.

It is another object of this invention to provide a stress management apparatus that is housed within a casing having the general appearance of a pulse oximeter that mounts on the fingertip of the user.

It is still another object of this invention to provide a stress management device that measures the user's pulse via use of a non-invasive infrared sensor.

It is a feature of this invention that the stress management apparatus can be positioned on the end of a finger of the user to detect stress levels through measurements of the user's pulse rate.

It is another feature of this invention that the stress level of the user can be calculated from the heart rate variability in the user's pulse rate, as detected through the infrared sensor.

It is an advantage of this invention that the stress management device is compact and can be carried easily on the person of the user for utilization as desired.

It is another advantage of this invention that the stress management apparatus incorporates a training procedure to conform the breathing pattern of the user into a low stress breathing pattern.

It is still another feature of this invention that the stress level of the user can be reduced through utilization of the stress management device and conforming to the training protocol provided by the stress management device.

It is still another object of this invention to provide an algorithm to measure the stress level of the user and then to provide feedback via a display screen on the stress management device to allow the user an opportunity to recognize stress levels and to adopt a breathing pattern that will reduce stress levels.

It is still another feature of this invention that the results of the stress measurement algorithm are displayed to the user at the end of the training period to provide feedback to the user as to the effectiveness of the efforts to reduce stress levels.

It is still another advantage of this invention that the results of the stress measurement algorithm are displayed in a pie chart reflecting the calculations of low, medium and high stress levels, as measured through the repeated application of the algorithm.

It is yet another feature of this invention that the stress management device provides a graphic to aid the user in establishing a breathing pattern that will lower the user's stress level.

It is yet another advantage of this invention that the graphic image displayed to the user is a diagram of a pair of lungs filling and emptying to urge the inhalation and exhalation of the user into a stress reducing breathing pattern.

It is a further feature of this invention to provide an integrated design for a stress management device that enables the measurement, display and power supply all gathered in a small finger clip device.

It is a further advantage of this invention to manage the respiration biofeedback of the stress management device by using animation to guide and display the user's current relaxation status.

It is yet a further advantage of this invention to provide a scoring method corresponding to the percentages of high, medium and low stress level scores calculated during the training period to encourage continued use of the stress relaxation techniques promoted by the stress management apparatus.

It is a further object of this invention to provide a stress management apparatus that is provided in a small, compact housing to promote a reduction of stress levels of the user through suggested breathing techniques resulting in scores to encourage stress reduction that is durable in construction, carefree of maintenance, and simple and effective in use.

These and other objects, features and advantages are accomplished according to the instant invention by providing a stress management device having an integrated design that enables pulse measurement, display of results and a power supply gathered into a small finger clip device. The stress management device includes an infrared sensor that identifies and measures pulse rate variability and utilizes that information to calculate the power spectrum distribution. The device incorporates a display screen on which a graphic image of a pair of lungs filling and emptying to encourage the user into a predetermined breathing pattern known to reduce stress levels during a training period. After the completion of the training period, the device presents a score reflecting the percentage of times the user achieved high, medium and low relaxation states, and a pie chart reflecting the distribution of the states of relaxation calculated during the training period.

BRIEF DESCRIPTION OF THE DRAWINGS

The foregoing and other objects, features, and advantages of the invention will appear more fully hereinafter from a consideration of the detailed description that follows, in conjunction with the accompanying sheets of drawings. It is to be expressly understood, however, that the drawings are for illustrative purposes and are not to be construed as defining the limits of the invention.

FIG. 1 is a schematic perspective view of a stress management device incorporating the principles of the instant invention;

FIG. 2 is another schematic perspective view of the stress management device shown in FIG. 1 to show the opening in which the finger of the user is inserted to enable a reading and measurement of the pulse rate variability of the user;

DETAILED DESCRIPTION OF THE PREFERRED EMBODIMENT

Figure 3:
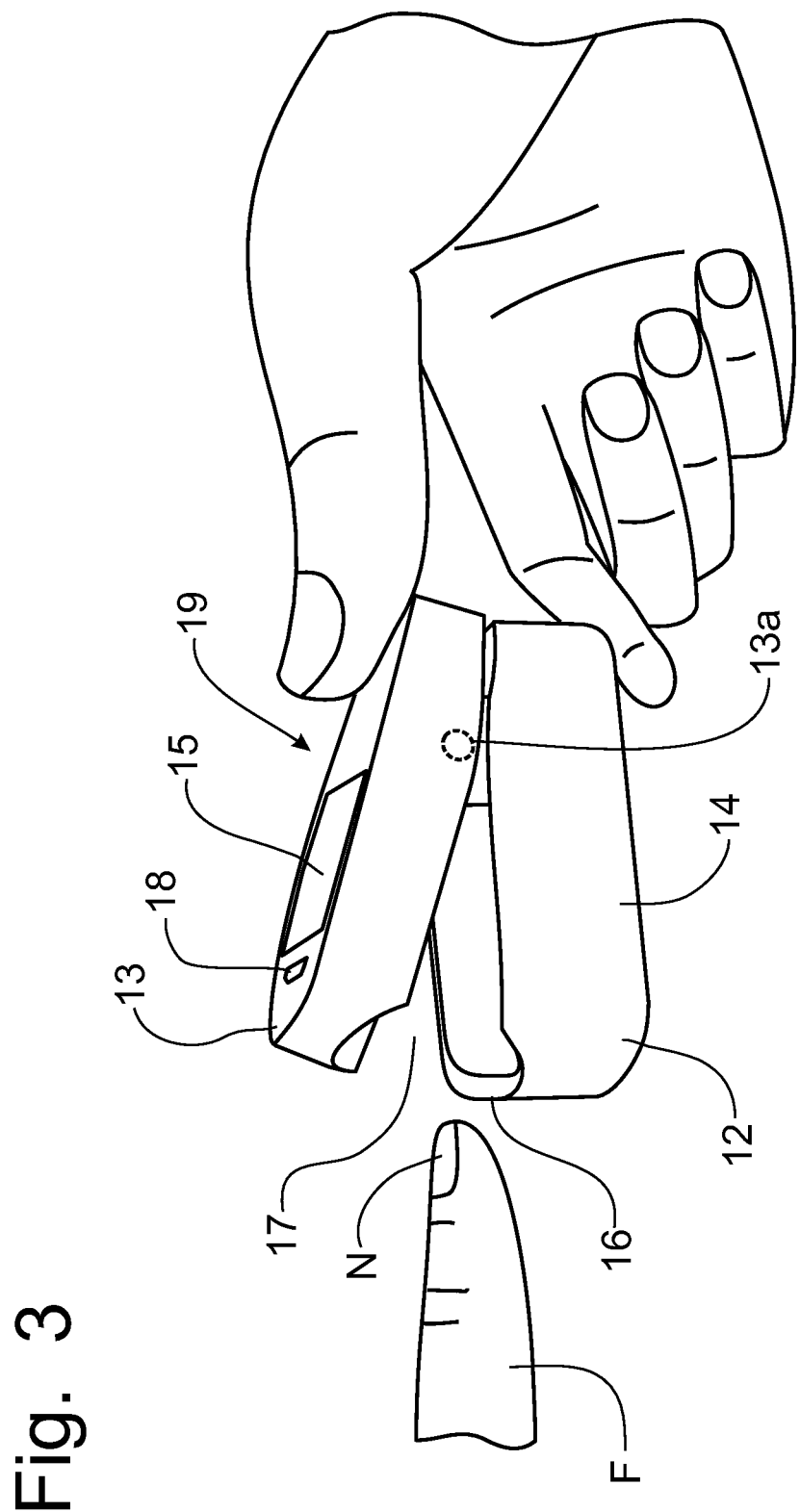
FIG. 3 is another schematic perspective view of the stress management device of FIGS. 1 and 2 to depict the application of the device onto a finger of the user.

Referring to FIGS. 1-3, a stress management device, incorporating the principles of the instant invention, can best be seen. This stress management device 10 combines breath guiding and heart rate variability biofeedback technology, by analyzing the signal detected from a non-invasive sensor 17 positioned on the finger to extract heart rate variability information and identify the coherence between heart rate variability and respiratory rhythm. In this manner, the device 10 can, therefore, monitor the status and degree of relaxation of the user. The stress management device 10 can be used to guide the user to breathe by an intuitive graphic display, and to help the user to focus his/her attention, as well as adjust his/her emotion actively, aiding the user to enter into a highly relaxed state of body and mind.

Figure 6:
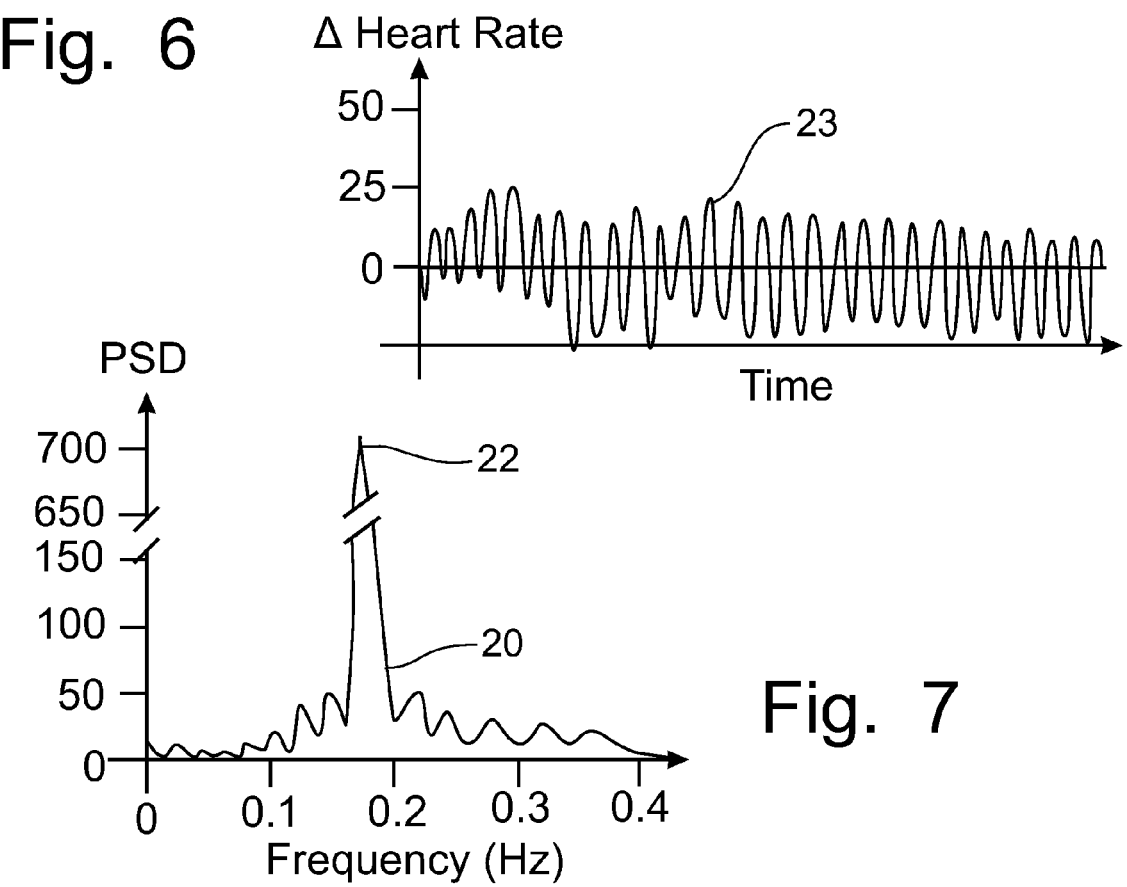
FIG. 6 is a representative graph of the heart rate variability curve measured through the infrared sensor in the upper portion of the device housing.
Figure 7:
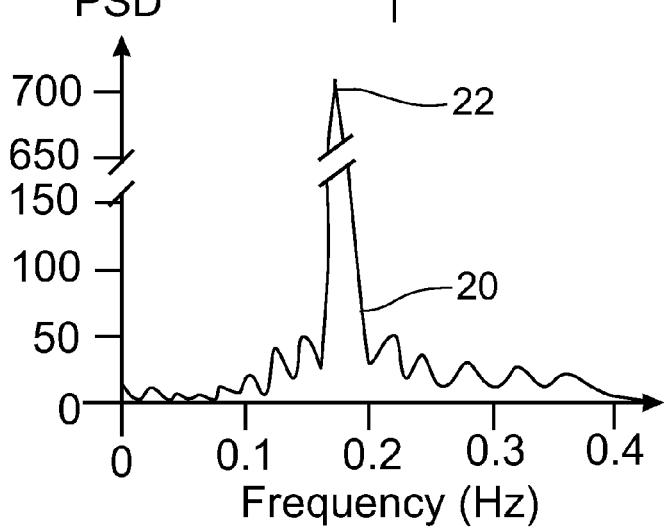
FIG. 7 is a representative graph of the power spectrum distribution developed from the heart rate variability graph.

The stress management device 10 includes a housing 12 that is formed similarly to a pulse oximeter, a device that is mounted on a user's fingertip to determine the pulse rate and oxygen content of the user's blood, such that there is an upper member 13 on which the display screen 15 is located and a lower member 14 pivotally hinged to the upper member 13 at the pivot 13a so that a user's finger F can be positioned within an opening 16 between the upper and lower members 13, 14. A multifunction button 18 is provided on the upper member 13 to allow a selection of a menu function, as will be described in greater detail below. A non-invasive photoelectric sensor, such as an infrared sensor 17 located in the upper and lower members 13, 14, detects the heart rate of the user through the user's fingernail N, in a similar manner as is accomplished through a pulse oximeter. Preferably, the infrared sensor 17 operates at a frequency of about one hundred times per second to identify and record the time interval between heart beats, as well as heart rate variability (HRV), which is re-sampled at a frequency of four times per second and corresponds to the time interval between the respective beats of the user's heart. The stress management device 10 then transforms the heart rate variability curve, such as is representatively depicted in FIG. 6, by utilizing the known process of the Fast Fourier Transform (FFT) algorithm to obtain a power spectrum distribution (PSD) curve 20, as is shown in FIG. 7.

Figure 5:
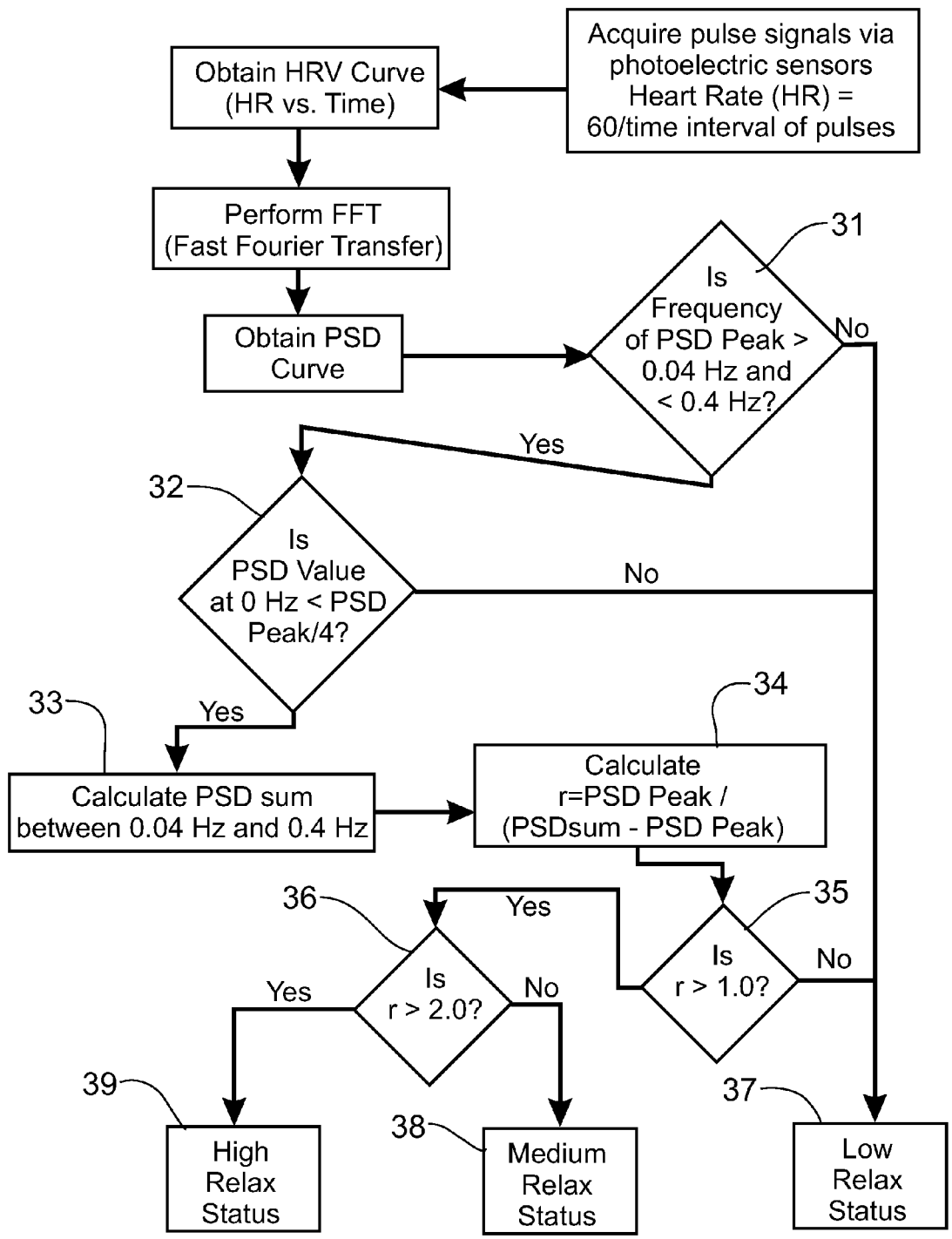
FIG. 5 is a logic flow diagram reflecting the algorithm for calculating the relaxation status of the user during the training period.

As is reflected in the logic flow diagram in FIG. 5, the PSD diagram 20 is then utilized by the processor 19 within the device 10 at step 31 to determine if the PSD curve 20 has a PSD peak 22 having a frequency falling between 0.04 and 0.4 cycles per second (Hz). If the PSD peak 22 is not in the designated range, the user is deemed to be in a low relaxed status at step 37. If the PSD peak 22 is within the designated range of 0.04 to 0.4 Hz, the processor 19 next checks at step 32 the PSD value reading from the PSD curve 20 at zero (0) Hz and compares the zero Hz PSD value reading to the PSD peak 22 reading divided by the number 4. If the PSD value reading at zero Hz is greater than 25% of the PSD peak 22, the user is deemed to be in a low relaxed status 37.

If the value of the zero Hz PSD value reading is less than the PSD peak 22 reading divided by 4, then the processor 19 calculates at step 33 the area beneath the PSD curve between the 0.04 and 0.4 cycles per second (Hz) boundaries, referred to as PSDsum. Then at step 34, the processor 19 calculates a ratio of the PSD peak 22 reading to PSDsum less the PSD peak 22 reading. At step 35, if that ratio calculation is less than 1.0, the user is deemed to be in a low relaxed status 37. At step 36, if the calculated ratio is greater than 2.0, the user is deemed to be in a high relaxed status 39, but if the calculated ratio is greater than 1.0, but less than 2.0, then the user is deemed to be in medium relaxed status 38. When the user is deemed to be in a medium relaxed status 38 or a high relaxed status 39, the respiration rate of the user can be calculated as being 60 times the frequency at the PSD peak 22.

The average heart rate for normal people is considered to be at 72 beats per minute, which corresponds to 0.833 seconds (or 833 milliseconds) between heart beats. Further, most people have a variation in their heart rate corresponding to respiration. The heart rate for most people increases when inhaling and decreases when exhaling. This variation in the heart rate corresponding to respiration typically averages in the range of 50-60 milliseconds for adults, and about 20-25 milliseconds for elderly people. Some studies have shown that there can be as much as 10% variability in the heart rate for a normal adult person. This variability in the heart rate is typically referred to by the acronym HRV and is reflected in FIG. 6. Accordingly, the sampling of the heart rate at four times per second by the stress management device 10 can result in the identification of when the user is inhaling and exhaling.

Figure 4:
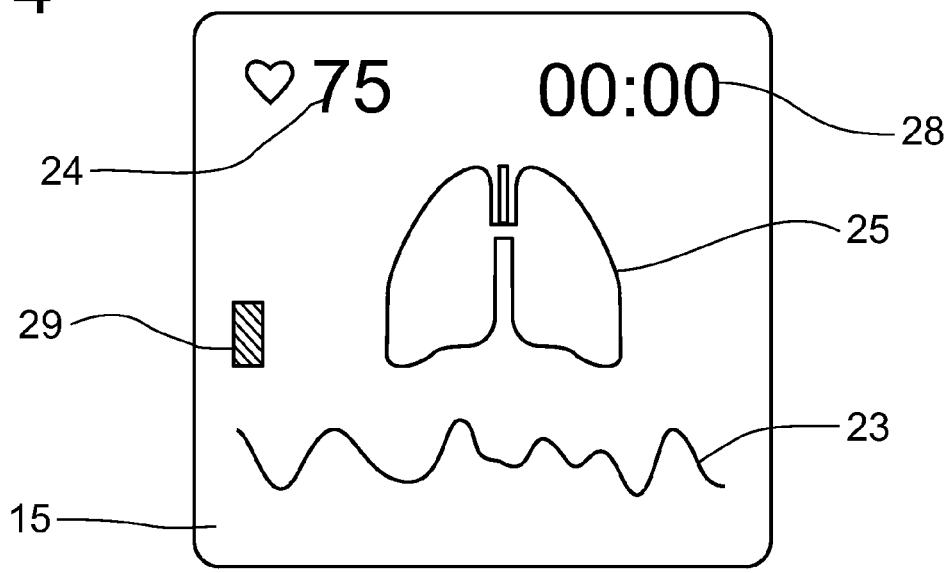
FIG. 4 is a schematic diagram of the display screen depicting the graphic images utilized to encourage the user into a suggested predetermined breathing pattern known to reduce stress levels.
Figure 4A:
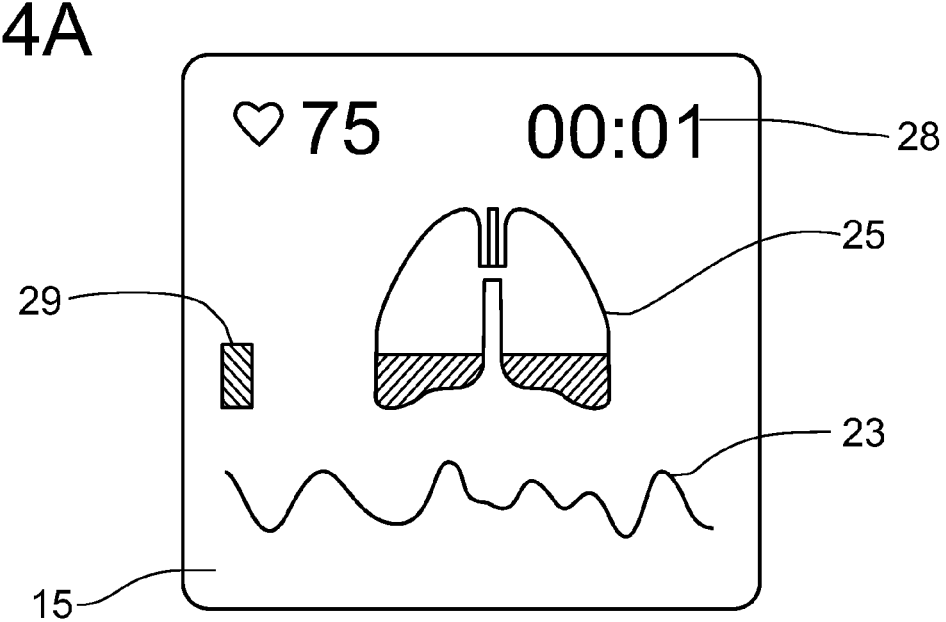
FIGS. 4A through 4E reflect the animated graphic image for encouraging the user into the predetermined breathing pattern.
Figure 4B:
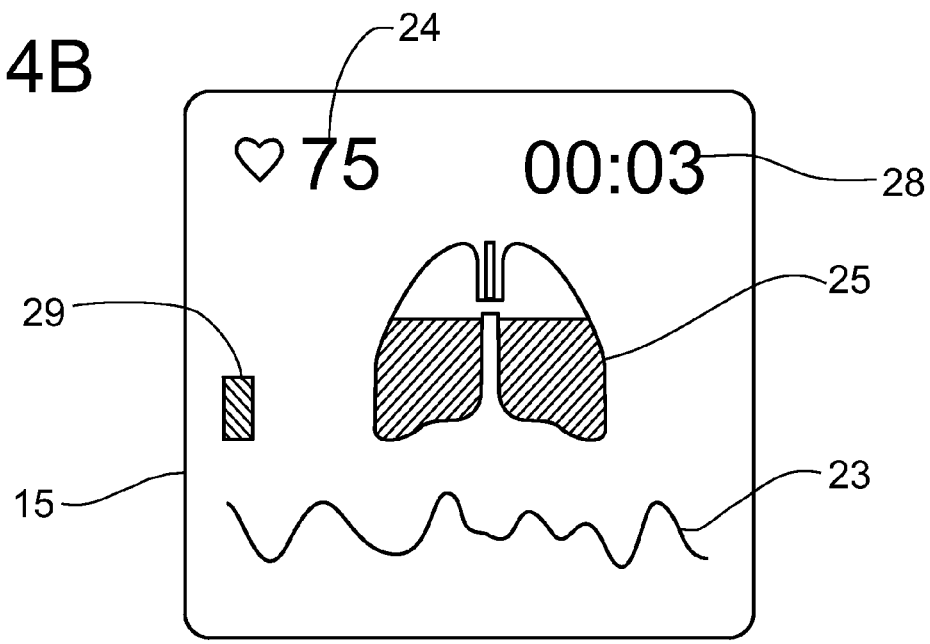
Figure 4C:
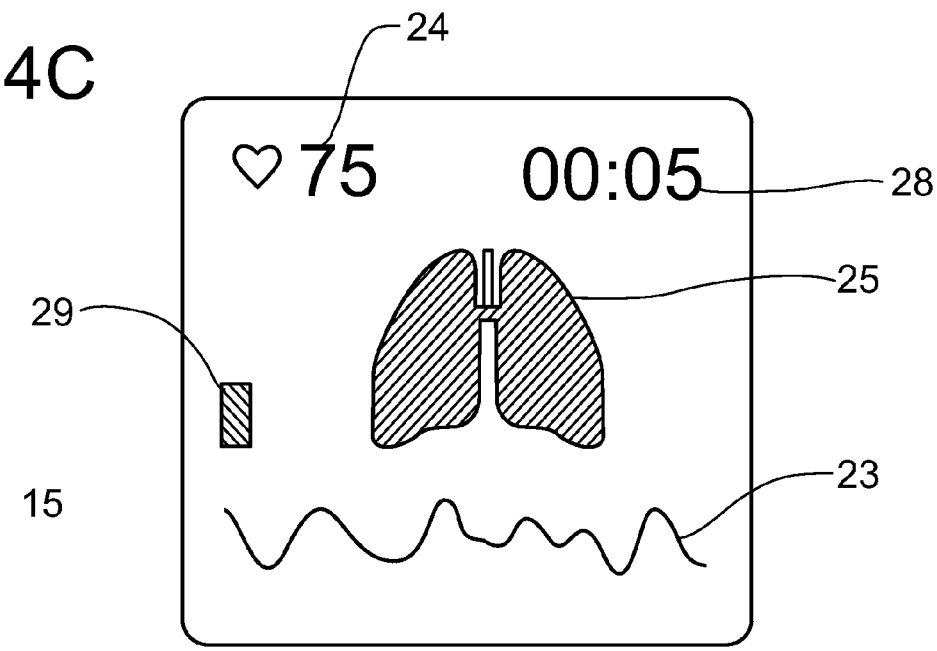
Figure 4D:
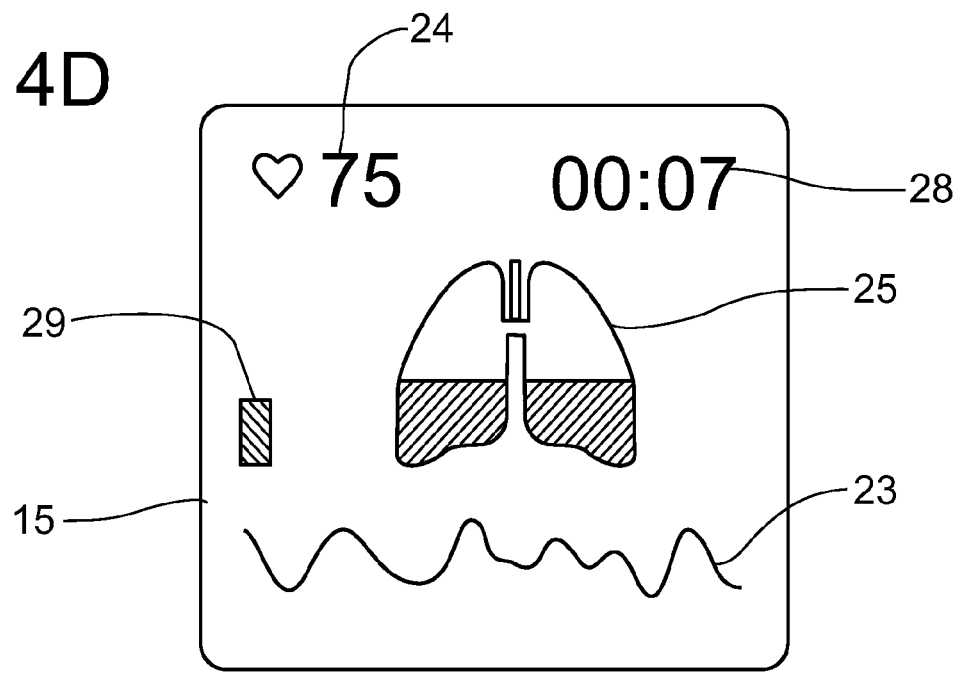
Figure 4E:
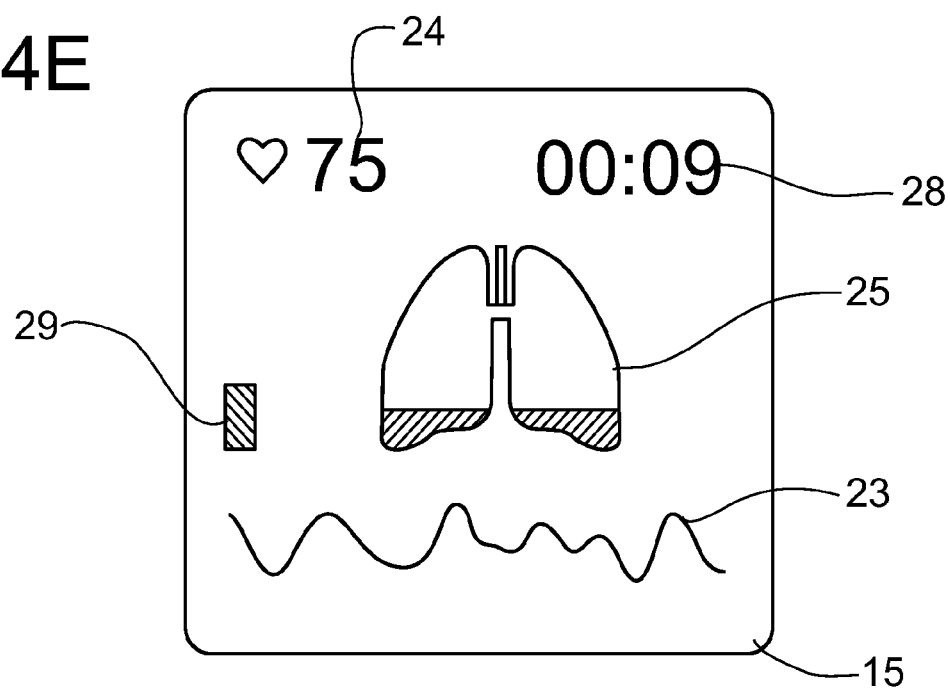

As noted above, maintaining a respiratory rate in the range of 5 to 10 breaths per minute, and specifically at 6 breaths per minute can result in a continuation of a high relaxed state. Accordingly, the stress management device 10 provides animation on the display screen 15 to help guide the user into a respiratory pattern that will help the user maintain a high relaxed status. As is depicted in FIG. 4, the display screen 15 can show an animated device 25, such as a graphic of a pair of lungs filling up and emptying at an interval corresponding to the preferred respiratory rate, such as at 6 breaths per minute with five seconds devoted to inhaling and five seconds devoted to exhaling, as is represented in FIGS. 4A through 4E. By attuning the user's respiratory pattern to the animation device 25, the user can achieve high relaxed status 39. The animated device 25 is displayed on the display screen 15 during the training period during which the user is urged to breathe in the pattern suggested by the animated device 25.

Figure 8:
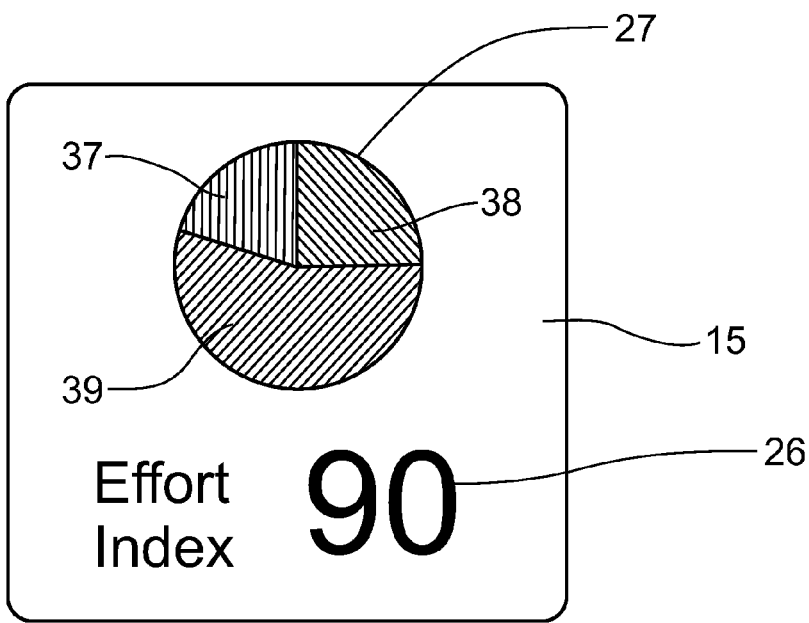
FIG. 8 is a schematic diagram of the display screen depicting the pie chart showing a representative distribution of the high, medium and low relaxation states of the user, along with an effort index score calculated from the percentages of the respective relaxation states.

After the training period provided by the stress management device 10, during which the processor 19 makes evaluations taken from the pulse readings twelve times each minute, the processor 19 makes a statistical evaluation of the fractions of high, medium and low related status corresponding to the determinations of low, medium and high relaxed status evaluations from the algorithm reflected in FIG. 5, and then derives an effort index score for the user from the fractions of high, medium and low relaxed status determinations. The computation of the effort index score 26, as depicted in FIG. 8, being equal to the fraction of the high relaxed status readings multiplied by 4 added to the fraction of the medium relaxed status readings multiplied by 3 and to the fraction of the low relaxed status readings multiplied by zero, the sum of which is divided by 4 and then multiplied by 100, with the total of the fractions of the high, medium and low relaxed status readings equaling 1.0. This score is then presented to the user on the display screen 15 as a motivation to achieve a greater percentage of high relaxed status readings 39. The fractions of the high, medium and low relaxed status readings can also be represented in a pie chart 27, as depicted in FIG. 8, in which the percentage of high relaxed status 39, medium relaxed status 38, and low relaxed status 37 are displayed graphically, to provide additional information and motivation for the user to utilize the stress management device 10 to achieve a greater percentage of high relaxed status readings 39. The greater the percentage of high relaxed state readings 39, compared to the medium relaxed state readings 38 and the low relaxed state readings 37, increases the effort index score 26.

As is best seen in FIG. 4, the display screen 15 displays a graphic image 25, preferably in the form of a pair of lungs filling and emptying with a color display, to guide the user in a suggested predetermined breathing pattern known to induce a high state of relaxation in the user. In addition, the display screen 15 can provide other important information to the user, including the heart rate 24, a timer 28 identifying the length of the training period, a color-coded indicator (not shown) that provides an instantaneous image showing the most recent relaxation state calculation, and a bar graph 29 that exhibits the strength of the detected pulsation of the user's heart beat. Preferably, the timer 28 will alternate every two or three seconds as a display with the color-coded indicator (not shown) that could display the color green for a high relaxation state, yellow or blue for a medium relaxation state and red for a low relaxation state. The timer 28 will preferably countdown from 60 to zero for the first minute of the training period because the effort index score requires a training period having a duration of at least one minute to provide a displayed result. After the timer 28 has counted down the first minute, the additional time of the training period will preferably be shown in increasing numbers. The training period can be as long as the user desires, although a maximum of twenty minutes is recommended, provided that the training period lasts for at least one minute.

In operation, the user will power up the stress management device 10 by simply placing the device 10 on his/her finger so that the non-invasive infrared sensor 17 can sense the heart beat of the user and initiate operation of the device 10. Preferably, the stress management device 10 will go through a training session in which the animated device 25 operates at a predetermined initial guided respiratory rate, such as a rate of six breaths per minute, to guide the user into a respiratory pattern that results in a high relaxed state 39. Preferably, the display screen 15 will show the heart rate variability (HRV) curve 23 in the form of a wave pattern. The heart rate variability curve 23 is an important indicator of physiological compliance and emotional flexibility. When the HRV curve 23 looks like a sinusoidal waveform, the HRV is stabilized and the user is relaxed. When the user experiences stressful emotions, the curve 23 becomes irregular and incoherent with the respiration pace.

If the user is uncomfortable with the demonstrated respiratory rate of six breaths per minute, the stress management device 10 will preferably have a function by which the user can change the guided respiration rate to a different predetermined initial guided respiratory rate. If the user feels that the guided respiration rate demonstrated by the animated device 25 is too slow for relaxation, the user can select a lower training level for breathing more comfortably. Similarly, if the user feels that the guided respiration rate is too fast, the user can select a higher training level to slow down the operation of the animated device 25. Optionally, the animated device 25 can also utilize an audible respiration guide to guide the respiratory pattern of the user rather than, or in addition to, the animated graphics.

After the user has followed the initial guided respiratory rate and the HRV is stabilized, which typically occurs in about 25 seconds, the stress management device 10 can adjust the guided respiration rate in response to the actual current respiration rate of the user. For example, if the current respiration rate of the user is greater than ten breaths per minute, the stress management device 10 can assist the user toward a higher state of relaxation by adjusting the guided respiration rate to equal the user's current respiration rate less a predetermined value, such as the number two. Once the respiration rate of the user has dropped below ten breaths per minute, the guided respiration rate can be adjusted to be equal to the user's actual current respiration rate. Meanwhile, the user is prompted to follow the guided respiratory rate displayed by the filing and emptying of the graphic lung image 25 on the display screen 15. In the alternative, the guided respiratory rate can be retained at the initial guided respiratory rate, or manually adjusted to a higher or lower rate as desired by the user.

When the user wants to obtain a relaxation score, the user will remove his/her finger F from the stress management device 10. If the training session has lasted for more than sixty seconds, the display screen 15 will preferably show a pie chart 27 indicating the percentages of the high, medium and low relaxed status readings 37-39, as well as a numerical score 26, calculated as defined above.

Preferably, the stress management device 10 will have a menu function stored and operated by the processor 19. By manipulating the multifunction button 18, the menu function can be selected to provide the user with a choice between high, mid or low training levels, with the mid-level training session corresponding to a respiratory rate of six breaths per minute. Also, the menu function can provide a selection for the use of the optional audible respiration guide. Alternatively, the multi-function button 18 can be configured to be used as a manual control for the on/off function of the device 10.

The stationary condition of breath and the trend of heart rate variation reflect the status of interaction between the sympathetic and parasympathetic neural system in the human body. When heart rate variation turns to be regular and synchronized with the breathing rhythm, it is considered that the neural system tends to be in harmony with the body and mind, which means that the physical body becomes more effective, the emotion turns more stationary, and the mind is peaceful and perceptive, which is called a highly physiological relaxed state. On the contrary, stressful emotions including anger, disappointment, and anxiety make the heart rate variation irregular and incoherent with breath. In this case, the stress management device 10 can be used to guide the user to conduct the slow and deep breaths, and help the user to focus his/her attention to enter into a relaxed state with body and mind in harmony.

This stress management device 10 combines the breathing guiding 25 and heart rate variability biofeedback 23 technology, by analyzing the signal detected from the non-invasive infrared sensor 17 on the finger and extracting the heart rate variability information 23 and the coherence between heart rate variability and respiratory rhythm, therefore, monitoring the status and degree of relaxation. The device can guide the user to breathe by an intuitive animated graphic display 25, and help the user to focus attention and adjust his/her emotion actively, aiding the user to enter into a highly relaxed state.

It will be understood that changes in the details, materials, steps and arrangements of parts which have been described and illustrated to explain the nature of the invention will occur to and may be made by those skilled in the art upon a reading of this disclosure within the principles and scope of the invention. The foregoing description illustrates the preferred embodiments of the invention; however, concepts, as based upon the description, may be employed in other embodiments without departing from the scope of the invention. The invention is not otherwise limited, except for the recitation of the claims set forth below.

Having thus described the invention, what is claimed is:

1. A method of inducing a high state of relaxation in a human being user comprising the steps of:

placing on a finger of the user a stress management device having a housing containing a display screen, a microprocessor and an infrared sensor that detects the pulse rate of the user when said housing is placed on the finger and from the detected pulse rate of the user generates a pulse rate signal that is sent to the microprocessor to compute a heart rate variability and a power spectrum distribution curve (PSD) corresponding to the heart rate variability, the power spectrum curve having a PSD peak value and an area value under the power spectrum distribution curve;

establishing a training period corresponding to the length of time the stress management device is positioned on the finger of the user;

checking the power spectrum curve to determine whether the frequency of the PSD peak value falls between 0.04 Hz and 0.4 Hz;

determining if the value on the power spectrum curve at zero Hz is less than 25% of the PSD peak value;

when both said checking and determining steps are positive, calculating a ratio of the peak value to the area value less the peak value;

utilizing the ratio to define the relaxation state of the user by predetermined ranges of said ratio to reflect a high relaxation state, a medium relaxation state and a low relaxation state; and when either of said checking and determining steps are negative, defining the relaxation state of the user as said low relaxation state and bypassing said calculating step.

2. The method of claim 1 wherein the stress management device comprises:

a housing having an upper member and a lower member pivotally connected to the upper member;

a non-invasive sensor mounted in one or both of a lower surface of said upper member and an upper surface of said lower member to detect a pulse rate when said housing is placed on a fingertip of a user with the fingertip being positioned between said upper and lower members and to provide pulse rate signals indicative of heart rate variability;

a microprocessor mounting in said housing to receive said pulse rate signals and to calculate a power spectrum distribution from said pulse rate signals, said power spectrum distribution being utilized by said microprocessor to determine a state of relaxation of the user; and a display screen supported on an upper surface of said upper member to provide visual indicators of the relaxation state of the user as determined by said microprocessor.

3. The method of claim 2 wherein said low relaxation state exists when the ratio is less than a first fixed value, said medium relaxation state exists when the ratio is greater than said first fixed value but less than a second fixed value, and said high relaxation state exists when the ratio is greater than said second fixed value.

4. The method of claim 3 wherein an effort index score is computed from respective corresponding percentages relating to attainment of the high relaxation state, the medium relaxation state, and the low relaxation state.

5. The method of claim 4 wherein said effort index score is displayed to the user on said display screen.

6. The method of claim 5 wherein a visual graph is also provided on said display screen to reflect the respective percentages of the high, medium and low relaxation states.

7. The method of claim 4 wherein said display screen includes a visual graphic representative of a suggested predetermined breathing pattern to induce a high relaxation state in the user while the device is placed on the fingernail of the user.

8. The method of claim 7 wherein the actual breathing pattern of the user is determined from the heart rate variability, a matching of the actual breathing pattern of the user to the suggested predetermined breathing pattern resulting in said high relaxation state.

9. The method of claim 2 wherein said non-invasive sensor comprises an infrared sensor mounted in said upper and lower members of said housing for association with the fingertip of the user.

10. The method of claim 1 further comprising the step of:
during the training period, displaying on the display screen a visual image reflecting a suggested predetermined breathing pattern to the user, said suggested predetermined breathing pattern reflecting said high relaxation state.

11. The method of claim 1 further comprising the step of:
after the completion of said training period, computing an effort index score reflecting a corresponding percentage of ratios established during the calculating step reflecting each of the high, medium and low relaxation states; and
displaying on said display screen the effort index score.

12. The method of claim 11 wherein said displaying also includes the step of:
further displaying a graphic chart on said display screen reflecting respective corresponding percentages relating to attainment of high, medium and low relaxation states established by said utilizing step during the training period.

13. The method of claim 1 wherein the ratio defined in said calculating step is compared to two fixed values, said low relaxation state being established if said ratio is less than a first fixed value, said high relaxation state being established if said ratio is greater than a second fixed value, said medium relaxation state being established if said ratio is greater than said first fixed value and less than said second fixed value.

14. A method of encouraging human being users to establish a high relaxation state, comprising the steps of:
placing on a finger of the user a stress management device having a housing containing a display screen, a microprocessor and an infrared sensor that detects the pulse rate of the user and generates a pulse rate signal sent to the microprocessor that calculates a heart rate variability and a power spectrum distribution (PSD) curve corresponding to the heart rate variability, the PSD curve having a PSD peak value and an area value under the PSD curve;
establishing a training period corresponding to the length of time the stress management device is positioned over the finger of the user;
checking the PSD curve to determine whether the frequency corresponding to the PSD peak value falls between 0.04 Hz and 0.4 Hz;
determining if the value on the PSD curve at zero Hz is less than 25% of the PSD peak value;
when both said checking and determining steps have positive results, calculating a ratio of the PSD peak value to the area value less the PSD peak value;
utilizing the ratio to define a high relaxation state, a medium relaxation state and a low relaxation state;
when either of said checking and determining steps produce negative results defining the relaxation state of the user as said low relaxation state without moving to said calculating step;
repeating said checking, determining, calculating and utilizing steps multiple times during said training period; and
providing visual feedback to the user on said display screen at the end of said training period to depict corresponding percentages of the high, medium and low relaxation states.

15. The method of claim 14 wherein the ratio defined in said calculating step is compared to two fixed values, said low relaxation state being established if said ratio is less than a first fixed value, said high relaxation state being established if said ratio is greater than a second fixed value, said medium relaxation state being established if said ratio is greater than said first fixed value and less than said second fixed value.

16. The method of claim 14 wherein said providing step includes the steps of:
after the completion of said training period, computing an effort index score reflecting corresponding respective percentages of ratios established during the calculating step reflecting each of the high, medium and low relaxation states;
displaying on said display screen the effort index score; and
further displaying a graphic chart on said display screen reflecting the respective percentages of high, medium and low relaxation states established by said utilizing step during the training period.

17. A method of encouraging human being users to establish a high relaxation state, comprising the steps of:
monitoring a user's heart rate variability during a training period by placing on a finger of the user a stress management device having a housing containing a display screen, a microprocessor and an infrared sensor that detects the pulse rate of the user and generates a pulse rate signal sent to the microprocessor that calculates a heart rate variability and a power spectrum distribution curve corresponding to the heart rate variability, the power spectrum distribution (PSD) curve having a PSD peak value and an area value under the power spectrum distribution curve;

determining the user's current respiratory rate;

establishing a guided respiratory rate that is less than the user's current respiratory rate by a predetermined fixed value when the user's current respiratory rate is greater than ten breaths per minute, the guided respiratory rate being equal to the user's actual respiratory rate when the user's current respiratory rate is less than or equal to ten breaths per minute;

prompting the user to breathe at the guided respiratory rate;

checking the power spectrum curve to determine whether the frequency corresponding to the PSD peak value falls between 0.04 Hz and 0.4 Hz;

determining if the value on the power spectrum curve at zero Hz is less than 25% of the PSD peak value;

when both said checking and determining steps have positive results, calculating a ratio of the PSD peak value to the area value less the PSD peak value;

utilizing the ratio to define the relaxation state of the user as one of a high relaxation state, a medium relaxation state and a low relaxation state; and when either of said checking and determining steps have negative results, defining the relaxation state of the user as said low relaxation state and bypassing said calculating step;

repeating said checking, determining, calculating and utilizing steps multiple times during said training period;

providing visual feedback to the user at the end of said training period to represent the states of relaxation for the user.

18. The method of claim 17 wherein said training period corresponds to the length of time the stress management device is positioned over the finger of the user.

19. The method of claim 17 wherein said step of providing visual feedback to the user includes the steps of:

after the completion of said training period, computing an effort index score reflecting corresponding respective percentages of ratios established during the calculating step reflecting each of the high, medium and low relaxation states;

displaying on said display screen the effort index score; and further displaying a graphic chart on said display screen reflecting the respective percentages of high, medium and low relaxation states established by said utilizing step during the training period.

20. The method of claim 17 wherein the ratio defined in said calculating step is compared to two fixed values, said low relaxation state being established if said ratio is less than a first fixed value, said high relaxation state being established if said ratio is greater than a second fixed value, said medium relaxation state being established if said ratio is greater than said first fixed value and less than said second fixed value.

21. The method of claim 17 wherein said step of establishing a guided respiratory rate comprises the steps of:

initializing the guided respiratory rate at a predetermined fixed value; and changing the guided respiratory rate after the heart rate variability of the user has stabilized according to the user's current respiratory rate being above or below ten breaths per minute.

22. The method of claim 21 wherein the predetermined value for adjusting the guided respiratory rate when the user's current respiratory rate is above ten breaths per minute is the number two.

23. The method of claim 17 wherein said prompting step includes the steps of:

during the training period, displaying on the display screen a visual image reflecting the guided respiratory rate to the user.

* * * * *